(12) United States Patent
Wang et al.

(10) Patent No.: US 6,768,053 B1
(45) Date of Patent: *Jul. 27, 2004

(54) OPTICAL FIBER ASSEMBLY

(75) Inventors: Xingwu Wang, Wellsville, NY (US); Bigang Min, Alfred Station, NY (US)

(73) Assignee: Nanoset, LLC, East Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/336,088

(22) Filed: Jan. 3, 2003

Related U.S. Application Data (63) Continuation-in-part of application No. 10/054,407, filed on Jan. 22, 2002, now Pat. No. 6,506,972.
(60) Provisional application No. 60/346,969, filed on Jan. 9, 2002.

(51) Int. Cl.[7] .............................................. H01B 11/06
(52) U.S. Cl. ............................................ 174/36; 333/12
(58) Field of Search ............................ 174/36, 102 SC; 333/12, 243; 523/300; 257/433

(56) References Cited

U.S. PATENT DOCUMENTS

| | | | | |
|---|---|---|---|---|
| 5,889,091 A | * | 3/1999 | Ziolo et al. | 523/300 |
| 6,281,489 B1 | * | 8/2001 | Tubel et al. | 250/227.14 |
| 6,310,381 B1 | * | 10/2001 | Taniguchi et al. | 257/433 |
| 6,506,972 B1 | * | 1/2003 | Wang | 174/36 |
| 2003/0080935 A1 | * | 5/2003 | Yang | 345/102 |

* cited by examiner

Primary Examiner—Chau N. Nguyen
(74) Attorney, Agent, or Firm—Howard J. Greenwald (57) ABSTRACT

A shielded assembly that includes a power source for generating electricity, a device for converting the electricity into optical energy, a device for converting the optical energy into electrical energy, and a load connected to the electrical energy. At least one lead connected to the load is shielded with nanomagnetic material.

19 Claims, 6 Drawing Sheets

OPTICAL FIBER ASSEMBLY

CROSS-REFERENCE TO RELATED PATENT APPLICATIONS

This application is a continuation-in-part of applicants' patent application U.S. Ser. No. 10/054,407, filed on Jan. 22, 2002, now U.S. Pat. No. 6,506,972.

This application also claims priority based upon provisional patent application U.S. Ser. No. 60/346,969, filed on Jan. 9, 2002.

FIELD OF THE INVENTION

An shielded optical fiber assembly comprised of means for converting electrical energy to optical energy, transferring such optical energy to a desired site, and then converting such optical energy back into electrical energy.

BACKGROUND OF THE INVENTION

In U.S. Pat. No. 5,549,642 of Xiaoyi Min et al., which is assigned to Medtronic, Inc., there is disclosed and claimed "An apparatus for delivering cardioversion pulses to the atrium of a patient's heart, comprising: means for sensing atrial tachyarrhythmia; a first electrode means for location in the coronary sinus of said patient's heart; a second electrode means for location in the right ventricle of said patient's heart; a third electrode means for location in the right atrium/superior vena cava portion of said patient's heart; means for coupling said first electrode means to said second electrode means; an implantable high voltage pulse generator having a housing and coupled to said first, second and third electrode means and including means for delivering a cardioversion pulse between said first and second electrode means while coupled to one another and said third electrode means, in response to a sensed occurrence of atrial tachyarrhythmia."

The device of U.S. Pat. No. 5,549,642 is comprised of pacemaker/cardioverter/defillibrator 110 and, connected thereto, lead bodies 115/116, each of which is comprised of a conductive material (such as, e.g., copper). These lead bodies, whose primary function is to conduct electricity to an implanted device near or in a heart, also act both as receiving and transmitting antennas. Consequently, when a patient in whom these leads 115/116 have been implanted is subjected to nuclear magnetic resonance imaging diagnosis, unwanted electromagnetic radiation will be absorbed, transformed, and/or emitted by leads 115/116.

U.S. Pat. No. 5,713,924 of Xiaoyi Min et al, which is also assigned to Medtronic, Inc., discloses and claims: "A device for providing a combined defibrillation therapy, comprising: pacing electrode means for delivering pacing energy pulse bursts to a first chamber of a patient's heart; defibrillation electrode means for delivering high energy pulses to said first chamber of said heart; means for detecting fibrillation in said first chamber of said heart; means for triggering delivery of said combined defibrillation therapy in response to detection of fibrillation in said first chamber of said heart; pacing pulse generator means responsive to said triggering means for delivering pacing energy pulse bursts having a frequency of 20 hz or greater to said pacing electrode means; defibrillation pulse generator means responsive to said triggering means for generating said high energy pulses for delivering a high energy pulse to said defibrillation electrode means in conjunction with each delivery of a said pulse burst to said pacing electrode means."

The device of U.S. Pat. No. 5,713,924 also contains conductive RA/SVC lead 140, and CS lead 130, each of which is comprised of conductive material, each of which serves to convey electricity to a device within or near a heart, and each of which also has the undesired property of acting as an emitting and/or receiving antenna;

In order to avoid the problem of using leads with conductive materials, some have proposed the use of an optical fiber delivering optical energy which can be converted into electrical energy prior to being delivered to an implanted device. However, the devices which have been proposed utilizing such optical fiber generally have poor power conversion efficiency.

It is an object of this invention to provide an optical fiber assembly that will convert electrical energy to optical energy, transfer such optical energy to a desired site, and then convert such optical energy back into electrical energy, all at a relatively high overall conversion efficiency.

SUMMARY OF THE INVENTION

In accordance with this invention, there is provided a shielded assembly comprised of a means for generating an electric current, means for converting said electric current to optical energy, means for converting said optical energy to electrical energy, and means for delivering electrical energy to a load, wherein said means for delivering said electrical energy to a load is coated with a composition comprised of at least about 50 weight percent of nanomagnetic material.

BRIEF DESCRIPTION OF THE DRAWINGS

The invention will be described by reference to the following drawings, in which like numerals refer to like elements, and in which.

DESCRIPTION OF THE PREFERRED EMBODIMENTS

Figure 1:
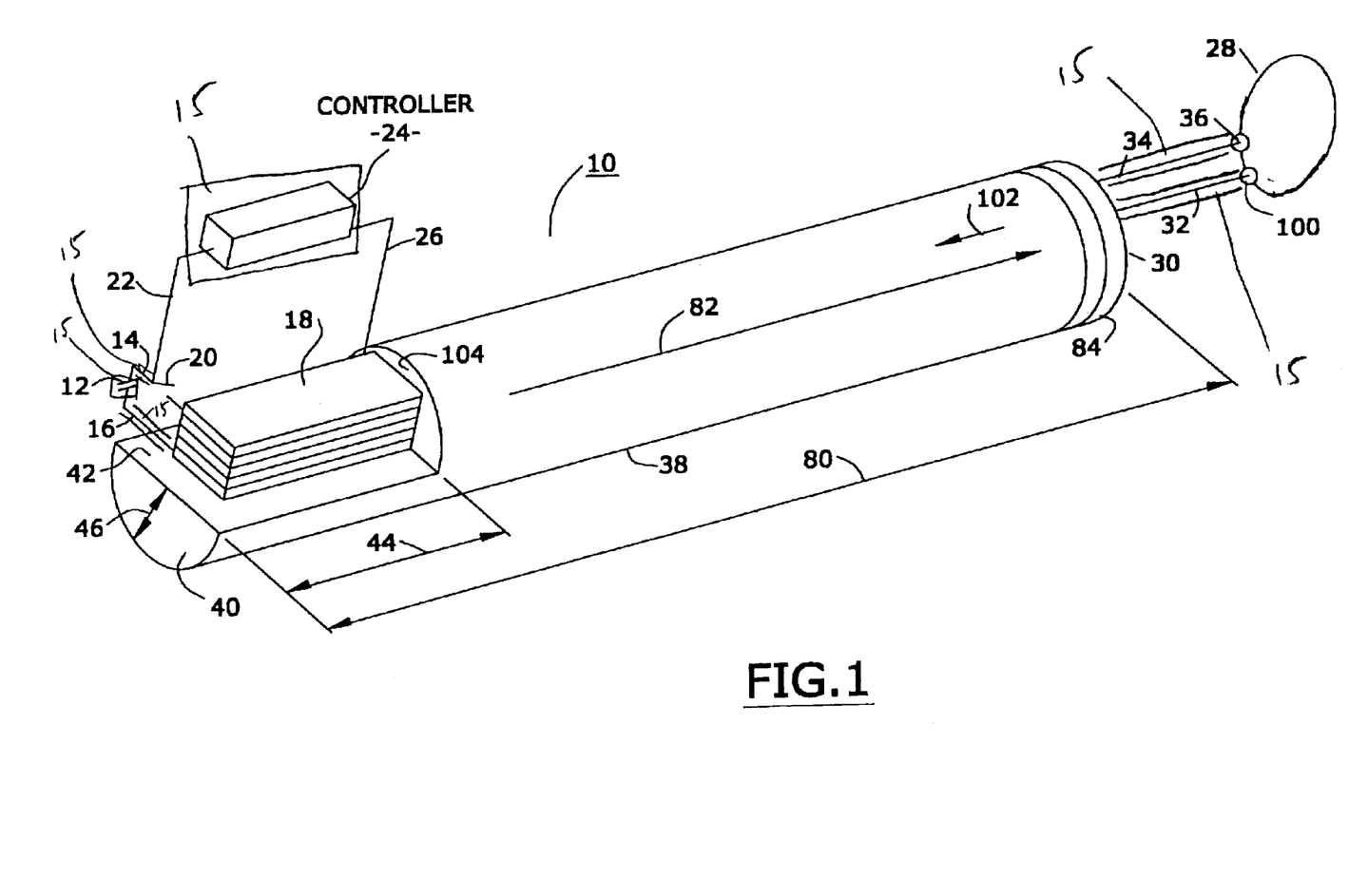
FIG. 1 is a schematic representation of one preferred optical fiber assembly of the invention.

Referring to FIG. 1, optical fiber assembly 10 is comprised of an electrical power source 12 that preferably delivers direct current; in the preferred embodiment depicted, electrical power source 12 has, disposed about it, a layer of nanomagnetic material 15. The nanomagnetic material may be contiguous with the power source 12; or a layer of non-nanomagnetic material may be disposed between the power source 12 and the nanomagnetic material layer 15.

The layer of nanomagnetic material 15, in one embodiment, is comprised of at least about 50 weight percent of nanomagnetic material. In another embodiment, the layer of nanomagnetic material 15 is comprised of at least about 90 weight percent of nanomagnetic material.

The power source 12 may, e.g., be a battery, a fuel cell, and the like.

In one embodiment, the power source 12 is a lithium-iodine or a lithium-bromine battery. By way of illustration and not limitation, one may use one or more of the lithium-halogen batteries patented by Wilson Greatbatch. Reference may be had, e.g., to U.S. Pat. Nos. 4,385,439 (lithium-iodine cell), 4,203,201, 4,128,703, 4,307,509 (lithium—chlorine cell), 4,210,708, 4,166,158, 4,164,070 (lithium—bromine battery), 4,132,836 (alkali metal—halogen cell), 4,105,833 (lithium—bromine cell), 3,994,747, 4,324,847 (lithium anode assemblies), 4,166,887, 4,111,721, 4,071,662, 4,058,889, and the like. The entire disclosure of each of these United States patents is hereby incorporated by reference into this specification.

Referring again to FIG. 1, the power from power source 12 is conveyed to leads 14 and 16 to light emitting device 18. The leads 14 and 16 should be relatively short. Thus, e.g., leads 14 and 16 are preferably no longer than about 1 centimeter. In one embodiment, leads 14 and 16 are less than about 1 millimeter.

In the embodiment depicted, each of the leads 14 and 16 is shielded by a layer 15 of nanomagnetic material that may either be contiguous with or not contiguous with the leads 14 and 16. In another embodiment, each of the leads 32 and/or 34 are also similarly shielded by a layer 15 of nanomagnetic material.

In one embodiment, leads 14 and/or 16, and/or battery 12 and/or leads 32 and/or 34, and/or controller 24 are coated with nanomagnetic material 15 which dissipates any magnetic fields produced by very high frequency radiation. As is known to those skilled in the art, this nanomagnetic material absorbs electromagnetic radiation. Typically, such nanomagnetic material contains iron, cobalt, and/or nickel. Reference may be had, e.g., to U.S. Pat. Nos. 5,889,091, 5,714,536, 5,667,924, 5,992,241, and the like. The entire disclosure of each of these United States patents is hereby incorporated by reference into this specification.

One may utilize the nanomagnetic material described in U.S. Pat. No. 6,506,972, the entire disclosure of which is hereby incorporated by reference into this specification. Alternatively, or additionally, one may use the assemblies comprised of nanomagnetic material that is described in such patent.

In one embodiment, one may utilize a magnetically shielded conductor assembly comprised of a first conductor disposed within an insulating matrix, and a layer comprised of nanomagentic material disposed around said first conductor, provided that such nanomagnetic material is not contiguous with said first conductor, wherein: (a) said first conductor has a resistively at 20 degrees Centigrade of from about 1 to about 100 micro ohm-centimeters, (b) said insulating matrix is comprised of nana-sized particles wherein at least about 90 weight percent of said particles have a maximum dimension of from about 10 to about 100 nanometers; (c) said insulating matrix has a resistively of from about 1,000,000,000 to about 10,000,000,000,000 ohm-centimeter; (d) said nanomagnetic material has an average particle size of less than about 100 nanometers; (e) said layer of nanmagnetic material has a saturation magnetization of from about 200 to about 26,000 Gauss and a thickness of less than about 2 microns; and (f) said magnetically shielded conductor assembly is flexible, having a bend radius of less than 2 centimeters.

In general, and as is known to those skilled in the art, nanomagnetic material is magnetic material which has an average particle size of less than 100 nanometers and, preferably, in the range of from about 2 to 50 nanometers. Reference may be had, e.g., to U.S. Pat. Nos. 5,889,091 (rotationally free nanomagnetic material), 5,714,136, 5,667,924, and the like. The entire disclosure of each of these United States patents is hereby incorporated by reference into this specification.

The nanomagnetic materials may be, e.g., nano-sized ferrites such as, e.g., the nanomagnetic ferrites disclosed in U.S. Pat. No. 5,213,851, the entire disclosure of which is hereby incorporated by reference into this specification. This patent claims a process for coating a layer of ferritic material with a thickness of from about 0.1 to about 500 microns onto a substrate at a deposition rate of from about 0.01 to about 10 microns per minute per 35 square centimeters of substrate surface, comprising the steps of: (a) providing a solution comprised of a first compound and a second compound, wherein said first compound is an iron compound and said second compound is selected from the group consisting of compounds of nickel, zinc, magnesium, strontium, barium, manganese, lithium, lanthanum, yttrium, scandium, samarium, curopium, terbium, dysprosium, holmium, erbium, ytterbium, lutetium, cerium, praseodymium, thulium, neodymium, gadolinium, aluminum, iridium, lead, chromium, gallium, indium, chromium, samarium, cobalt, titanium, and mixtures thereof, and wherein said solution is comprised of from about 0.01 to about 1,000 grams of a mixture consisting essentially of said compounds per liter of said solution; (b) subjecting said solution to ultrasonic sound waves at a frequency in excess of 20,000 hertz, and to an atmospheric pressure of at least about 600 millimeters of mercury, thereby causing said solution to form into an aerosol; (c) providing a radio frequency plasma reactor comprised of a top section, a bottom section, and a radio-frequency coil; (d) generating a hot plasma gas within said radio frequency plasma reactor, thereby producing a plasma region; (e) providing a flame region disposed above said top section of said radio frequency plasma reactor; (f) contacting said aerosol with said hot plasma gas within said plasma reactor while subjecting said aerosol to an atmospheric pressure of at least about 600 millimeters of mercury and to a radio frequency alternating current at a frequency of from about 100 kilohertz to about 30 megahertz, thereby forming a vapor; (g) providing a substrate disposed above said flame region; and (h) contacting said vapor with said substrate, thereby forming said layer of ferritic material.

By way of further illustration, one may use the techniques described in an article by M. De Marco, X. W. Wang, et al. on "Mossbauer and magnetization studies of nickel ferrites" published in the Journal of Applied Physics 73(10), May 15, 1993, at pages 6287–6289.

Typically, in a traditional pacemaker, the voltage required is about 5 volts, and the current required is about 10 milliamperes. In general, with such pacemaker, direct current pulses are delivered with a pulse duration about 0.5 milliseconds and a separation between adjacent pulses of about 0.7 seconds (based upon a pulse rate of about 80 heart beats per minute).

In the assembly 10 depicted in FIG. 1, pulsed energy can be provided to the assembly by means of switch 20, which is connected by line 22 to controller 24. Information from the assembly 10 is fed to the controller 24 via line 26. Upon receipt of such information, the controller may choose to open switch 20 and/or to close switch 20 at a rate or rates designed to produce the desired pulsed energy input to the heart 28.

The heart 28 receives electricity from distal end 30 of assembly 10 by means of line 32. The heart 28 returns information to assembly 10 by means of line 34, which is optically connected to a sensor 36 in or near such heart. Such information is conveyed through such line 34, to line 26, and then to controller 24, wherein it is evaluated.

The assembly 10, in one embodiment, is comprised of an optical fiber 38 which, preferably, is a low-loss optical fiber. The proximal end 40 of the optical fiber 38 is comprised of a platform 42. Disposed on such platform 42 is emitter 18.

The platform 42 typically has a length 44 of less than about 200 microns, and preferably less than about 100 microns. The height 46 of platform 42 is generally less than about 100 microns, and more preferably less than about 50 microns. The aspect ratio of platform 42, the ratio of its length 44 divided by its height 46, is generally greater than about 1.5.

The emitter 18 is preferably a laser diode assembly that is grown on the platform 42. Such a laser diode assembly may be grown on the platform 42 by conventional means. Reference may be had, e.g., to U.S. Pat. Nos. 5,538,918, 5,696,023, 5,567,980, 5,425,043, 5,262,360, 5,185,289, and the like. The entire disclosure of each of these United States patents is hereby incorporated by reference into this specification.

A process for growing an edge-emitting laser diode is described in a book by Govind P. Agrawal entitled "Fiber-Optic Communication Systems," Second Edition (John Wiley & Sons, Inc., New York, N.Y., 1997). At page 100 of such text, in FIG. 3.15(b), an etched-mesa buried heterostructure comprised of InGasAsP material is described.

Reference also may be had to William B. Jones Jr.'s "Introduction to Optical Fiber Communication Systems" (Oxford University Press, New York, N.Y., 1998). At page 147 of such book, in FIG. 5.42, a cross-section of an N-n-P double heterostructure edge-emitting LED is presented; and reference is made to "Semiconductor Devices for Optical Communication, H. Krseel, editor, Topics in Applied Physics, volume 39, second edition, Springer-Verlag, Inc., Heidelberg." At page 146 of such book, in FIG. 5.4.1(b) an edge-emitting LED is depicted. As is known to those skilled in the art, the same device can operate as either an LED or a laser diode, depending upon the amount of current delivered to the device. Below the threshold of the linear region, the device operates as an LED; above such threshold, the device operates as a laser diode.

By way of further illustration, reference also may be had to Christopher C. Davis' "Lasers and Electro-Optics: Fundamentals and Engineering" (Cambridge University Press, Cambridge, England, 1996). At page 303 of this text, in FIG. 13.33(a), a gallium-aluminum-arsenic double heterojunction DFB laser structure is depicted; and a cross-sectional view of this device is presented in FIG. 13.33(b). This device is an edgemitting laser diode.

Figure 3A:
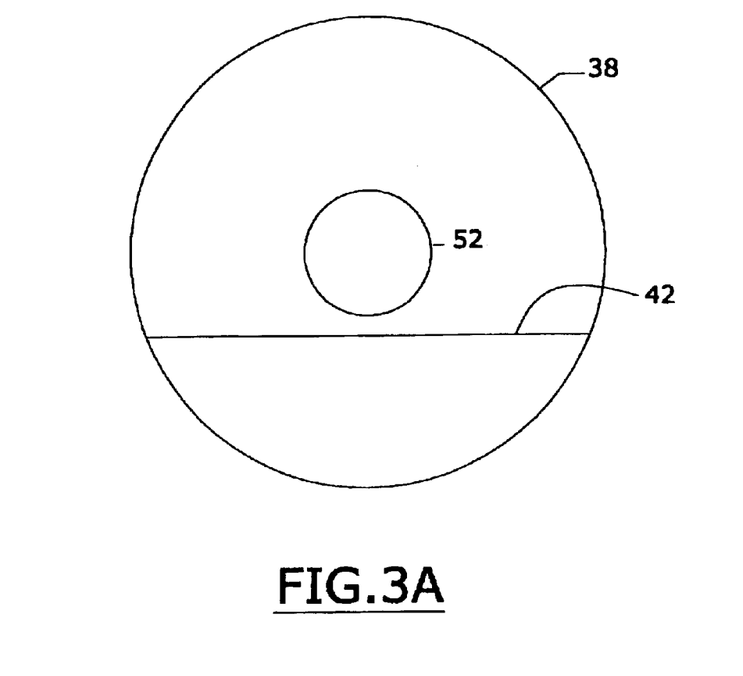
FIGS. 3A and 3B are sectional views, taken along lines 3-3' of FIG. 2, of the optical fiber assembly of FIG. 1.
Figure 3B:
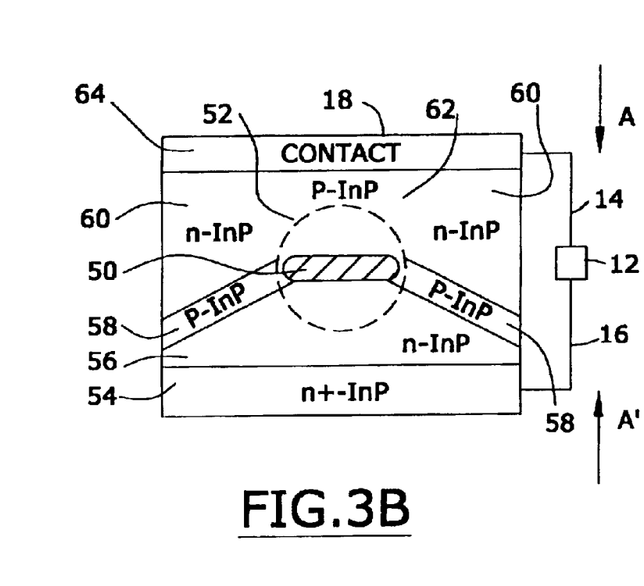

Referring again to FIG. 1, and in the preferred embodiment depicted therein, the light-emitting laser diode 18 is preferably comprised of a multiplicity of layers of material, which are shown in better detail in FIG. 3B.

Referring to FIG. 3B, it will be seen that edge-emitting laser diode 18, in the embodiment depicted, is comprised of active region 50, from which light is emitted. In one preferred embodiment, this active region 50 is an InGaAsP material, such as the material depicted, e.g., in FIG. 3.15(b) of the Agrawal text, supra.

Referring again to FIG. 3B, the active region 50 is preferably contiguous with the core 52 of the optical fiber 38. This relationship is shown in different detail in FIGS. 3A and 3D.

Referring again to FIG. 3B, it will be seen that device 18 is comprised of base 54, which preferably contains over-doped negative InP material; layer 56, which preferably contains negative InP material; layer 58, which contains positive InP material, layer 60, which contains negative InP material; mesa layer 62, which contains positive InP material, and contact 64, which contains conductive material and makes electrical contact with lead 14. As will be apparent to those skilled in the art, edge-emitting laser diodes using other semicondcutive materials also may be constructed. Thus, e.g., the edge-emitting laser diode depicted in FIG. 3C is similar to the diode shown on page 147 of the aforementioned Jones book.

Figure 3C:
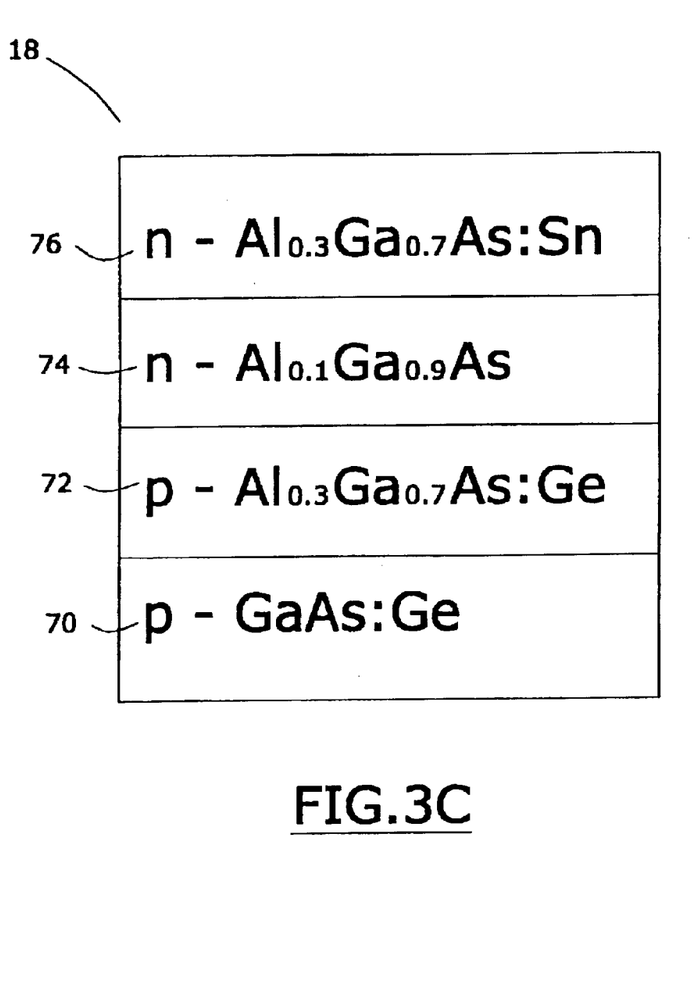
FIG. 3C is a perspective view of the light emitting assembly of the optical fiber assembly of FIG. 1.
Figure 3D:
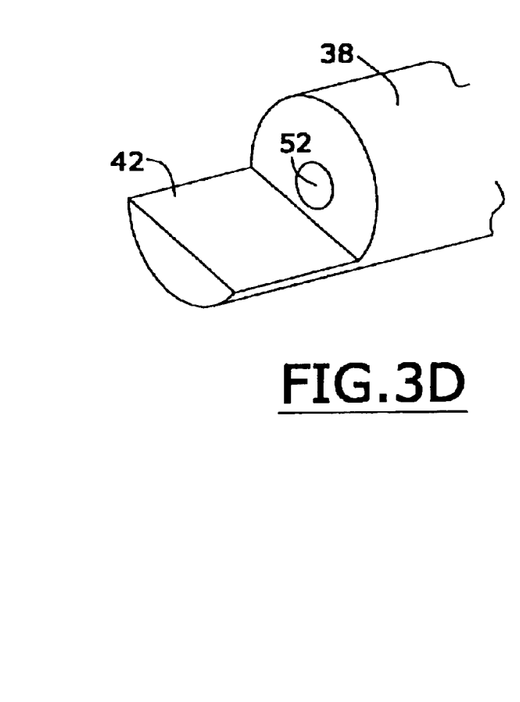
FIG. 3D is a partial perspective view of the proximal end of the optical fiber assembly of FIG. 1.

Referring to FIG. 3C, and in the preferred embodiment depicted, the edge emitting laser diode 18 consists of four major layers. The first layer, layer 70, comprises positive GaAs:Ge material. The second layer, layer 72, comprises positive $Al_{0.3}Ga_{0.7}As$:Ge material. The third layer, layer 74, is a negative (active) layer and comprises $Al_{0.1}Ga_{0.9}As$ material. The fourth layer, layer 76, is a negative layer comprising $Al_{0.3}Ga_{0.7}As$:Sn material.

Referring again to FIG. 1, the edge-emitting laser diode, in response to current delivered by power source 12, will produce light whose intensity and duration varies with the intensity and duration of the electrical input signal(s). This light is then transmitted down the length of optical fiber 38, through its core 52.

The optical fiber 38 preferably has a length 80 of less than about 12 inches when utilized in conjunction with a pacemaker. The fiber 38 preferably is flexible; and it is preferably biocompatible with living organisms in which it is implanted.

The light beams 82 emitted from edge-emitting laser diode 18 travel to the distal end 30 of the fiber 38, where they contact photodetector assembly 84.

The photodetector assembly 84 is adapted to convert photonic energy into electrical energy. It preferably is a photovoltaic sensor. Such photovoltaic sensors are well known to those skilled in the art. Reference may be had, e.g., to U.S. Pat. Nos. 6,274,860, 5,800,631, 5,508,205, 5,474, 621, and the like. The entire disclosure of each of these United States patents is hereby incorporated by reference into this specification.

By way of further illustration, U.S. Pat. No. 6,331,673 describes a solar cell module which responds to wavelengths over a wide spectrum. By comparison, in the preferred embodiment depicted in FIG. 1, the photodetector 84 preferably has a peak response to photonic radiation in the wavelength range of from about 400 to about 1,600 nanometers; and the optical radiation 82 preferably is within such range and more preferably has a wavelength either from about 800 to about 900 nanometers, or from about 1250 to about 1400 nanometers, or from about 1500 to about 1600 nanometers. The use of one of these frequency ranges maximizes the efficiency of the process.

By way of further illustration, U.S. Pat. No. 5,824,566 discloses a method for producing a photovoltaic device which contains a multiplicity of layers. As is the case with U.S. Pat. No. 6,331,773, the input to the photovoltaic device of this patent spans a relatively large range of wavelengths.

Figure 2:
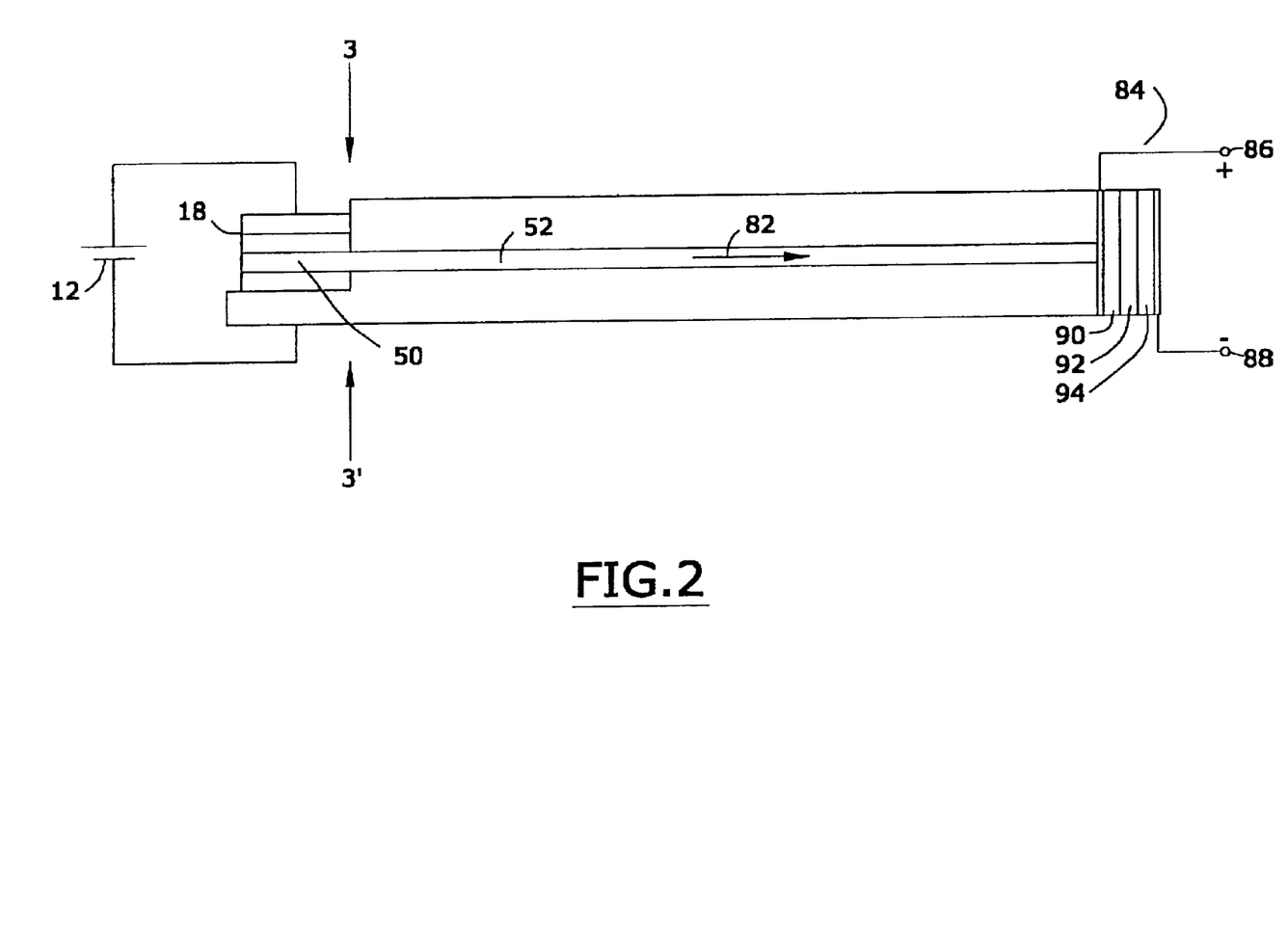
FIG. 2 is a partial schematic view of a portion of the optical fiber assembly of FIG. 1.

FIG. 2 illustrates the construction of a typical photovoltaic detector 84. Referring to FIG. 2, and in the preferred embodiment depicted, it will be seen that detector 84 is comprised of 3 major layers of material. Layer 90 is a positive AlGaAs-containing material. Layer 92 is a positive GaAs material. Layer 94 is a negative GaAs material. Light contacting this detector 84 provides a difference of potential between points 86 and 88.

Referring again to FIG. 1, the electrical energy produced by photovoltaic device 84 is transmitted via line 32 to a pacemaker 100. Information from such pacemaker is returned via line 34 to controller 24 in the manner described elsewhere in this specification.

In one embodiment, the return signal from line 34 sitmulates a photodetector (not shown) to provide a reverse light pulse 102 which, when it contacts another photodetector (not shown) near the face 104 of the platform 42, will cause a return electrical signal to be furnished to the controller 24 via line 26.

Figure 1A:
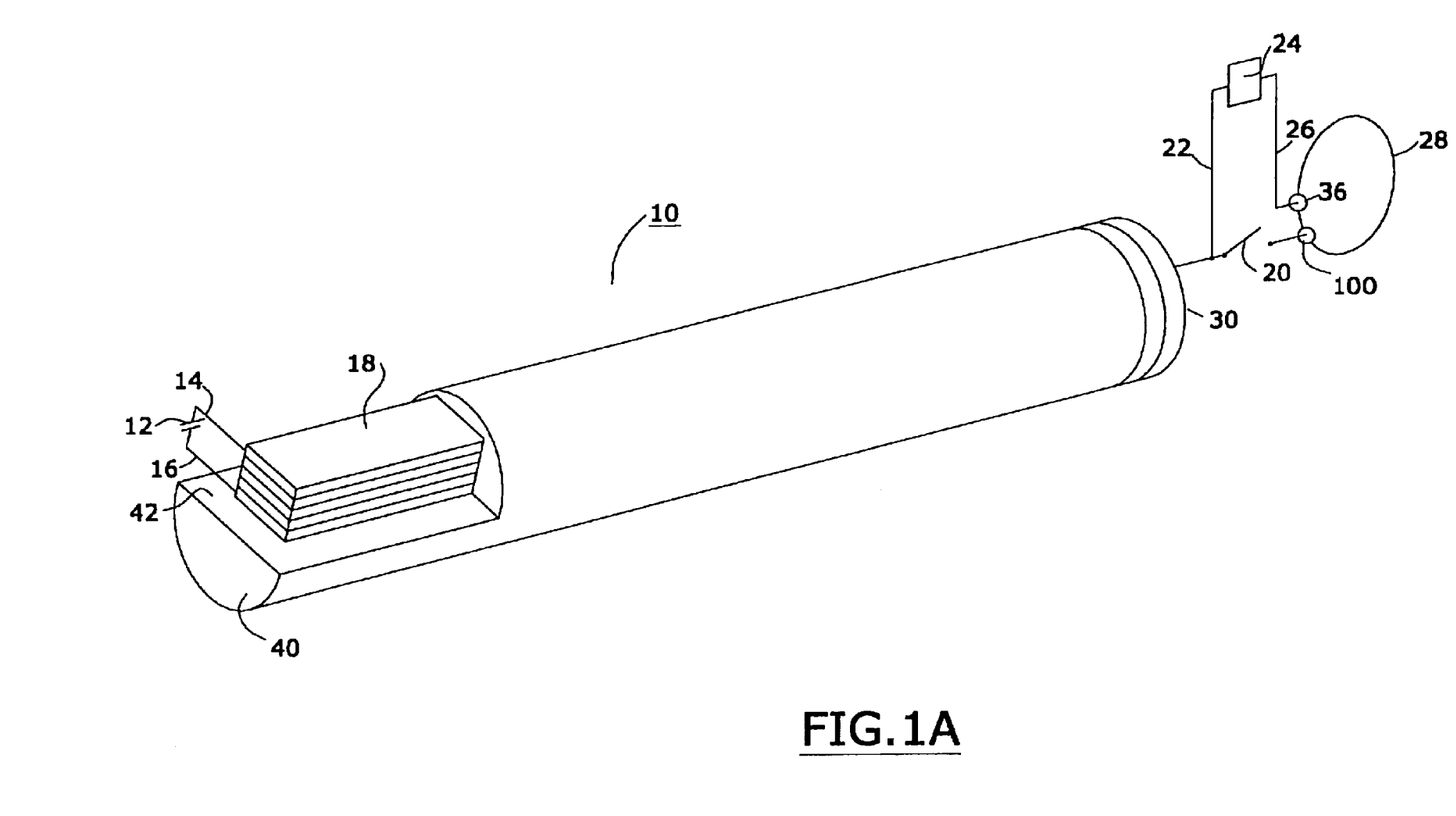
FIG. 1A is a schematic representation of another preferred optical fiber assembly of the invention.

FIG. 1A depicts an arrangement similar to that depicted in FIG. 1, with the exception that the controller 24 is disposed nearer the distal end 30 of the fiber 38 than the proximal end 40 of such fiber. As will be apparent to those skilled in the art, this arrangement utilizes shorter signals paths than the arrangement depicted in FIG. 1.

FIG. 2 is a sectional view of the assembly of FIG. 1.

Figure 4:
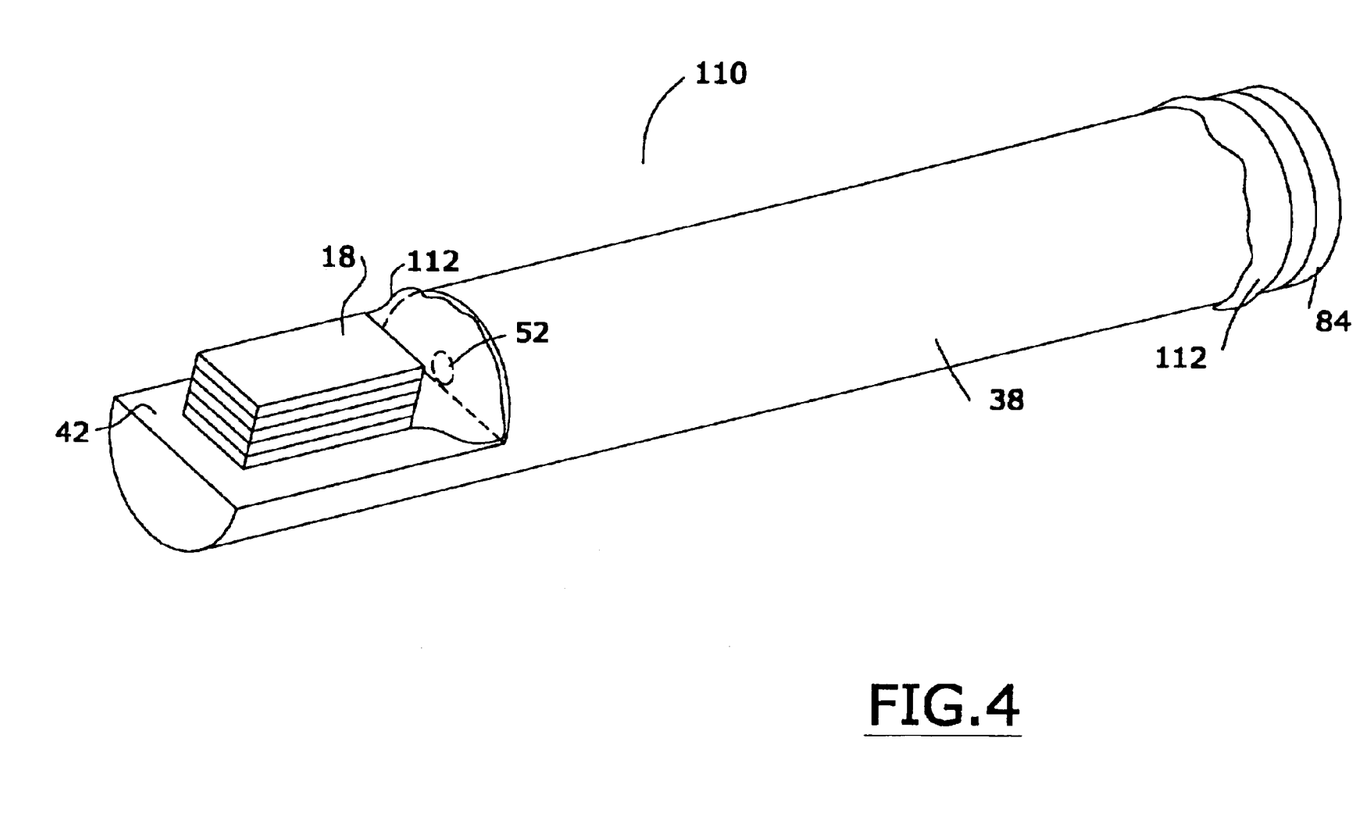
FIG. 4 is a perspective view of another preferred optical fiber assembly of the invention.

FIG. 4 is a perspective view of an optical fiber assembly 110 which is similar to the configuration depicted in FIG. 1 with the exception that the laser diode 18 is not contiguous with the core 52 of the optical fiber 38. In this embodiment, in order to maximize the efficiency of the device, an intermediate region 112 is used to match the index of refraction of the laser diode 18 and the core 52.

If there were not an intermediate section 112 between laser diode 18 and fiber core 52, the resulting air gap would not effectively couple the light emitter to the fiber core. In order to effectuate such coupling, one needs either contiguity (see FIG. 1), or an intermediate portion with an index of refraction substantially between the index of refraction of the active region of the laser diode 18, and the index of refraction of the fiber core 52. In one embodiment, the intermediate portion 112 will have an index of refraction of from about 1.4 to about 3.7. This "source-fiber coupling" is described on pages 123 et seq. of the aforementioned Agrawal text. On page 123, an index-matching liquid is mentioned. In one preferred embodiment, an index-matching epoxy material is used.

Reference also may be had to page 557 of the aforementioned Davis text, which discloses the use of an index matching fluid between two devices to minimize the Fresnel loss.

Referring again to FIG. 4, the photodetector assembly 84 depends upon absorption of light in wavelength bands. Different materials respond best in different ranges of wavelengths. At page 140 of the Agrawal text, the wavelength dependence of the absorption coefficient for several semiconductor materials are shown.

Thus, as will be apparent, as the material(s) within the detector 84 changes, the wavelength of the light emitted by emitter 18 also preferably changes to maximize the conversion efficiency. In order to effectuate such a change of emitted wavelengths, one may change the material used to construct emitter 18.

In one embodiment, depicted in FIG. 4, an index matching material 112 is disposed between the end of the optical fiber 38 and a separate photodetector 84. Without such an intermediate material 112, the air gap that would be present would decrease conversion efficiency. Reference may be had, e.g., to the "Laser Focus World Buyer's Guide 2001," Volume 36, issue 12, published by Laser Focus World of Tulsa, Okla. This guide presents a series of tables for semiconductor lasers which describes, for any particular desired wavelength, the output power, the threshold current, the laser mode, the rise time, the spectral width, the beam diverge, other special features, and the manufacturer. Thus, for any desired wavelength, one can choose the appropriate manufacturer(s) and the appropriate material(s).

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

We claim:

1. A shielded assembly comprised of a means for generating an electric current, means for converting said electric current to optical energy, means for converting said optical energy to electrical energy, and means for delivering said electrical energy to a load, wherein said means for delivering said electrical energy to said load is coated with a composition comprised of at least about 50 weight percent of nanomagnetic material, and wherein said nanomagnetic material has a particle size of less than about 100 nanometers, further comprising a controller.

2. The shielded assembly as recited in claim 1, wherein said composition comprised of at least about 50 weight percent of nanomagnetic material is disposed in a layer of nanomagnetic material comprised of at least 50 weight percent of said nanomagnetic material.

3. The shielded assembly as recited in claim 2, wherein said layer of nanomagnetic material has a thickness of less than about 2 microns.

4. The shielded assembly as recited in claim 3, wherein said layer of nanomagnetic material has a saturation magnetization of from about 200 to about 26,000 Gauss.

5. The shielded assembly as recited in claim 4, wherein said means for delivering said electrical energy to said load is a lead.

6. The shielded assembly as recited in claim 5, wherein said load is a pacemaker.

7. The shielded assembly as recited in claim 1, wherein said nanomagnetic material has an average particle size of from about 2 to about 50 nanometers.

8. The shielded assembly as recited in claim 1, further comprising a switch.

9. The shielded assembly as recited in claim 8, further comprising a sensor.

10. The shielded assembly as recited in claim 1, comprising an optical fiber.

11. The shielded assembly as recited in claim 10, wherein said optical fiber is a low-loss optical fiber.

12. The shielded assembly as recited in claim 11, wherein said optical fiber is comprised of a platform.

13. The shielded assembly as recited in claim 12 wherein, disposed on said platform, is an emitter.

14. The shielded assembly as recited in claim 13, wherein said emitter is a laser diode assembly.

15. The shielded assembly as recited in claim 14, wherein said emitter is comprised of a multiplicity of layers of material.

16. The shielded assembly as recited in claim 15, further comprising means for producing light with variable intensity and duration.

17. The shielded assembly as recited in claim 16, wherein said optical fiber has a length less than about 12 inches.

18. The shielded assembly as recited in claim 17, wherein said optical fiber is flexible.

19. The shielded assembly as recited in claim 18, wherein said optical fiber is biocompatible.

* * * * *